(12) United States Patent
Wallström et al.

(10) Patent No.: US 11,161,909 B2
(45) Date of Patent: Nov. 2, 2021

(54) REGIMENS AND METHODS OF TREATING MULTIPLE SCLEROSIS USING OFATUMUMAB

(71) Applicant: Novartis AG, Basel (CH)

(72) Inventors: Erik Wallström, Basel (CH); Marina Savelieva Praz, Binningen (CH); Algirdas Jonas Kakarieka Weisskopf, Basel (CH); Joseph Michael Kahn, Belle Mead, NJ (US)

(73) Assignee: NOVARTIS AG, Basel (CH)

(*) Notice: Subject to any disclaimer, the term of this patent is extended or adjusted under 35 U.S.C. 154(b) by 141 days.

(21) Appl. No.: 16/324,619

(22) PCT Filed: Aug. 11, 2017

(86) PCT No.: PCT/IB2017/054909
§ 371 (c)(1),
(2) Date: Feb. 11, 2019

(87) PCT Pub. No.: WO2018/033841
PCT Pub. Date: Feb. 22, 2018

(65) Prior Publication Data
US 2019/0177424 A1 Jun. 13, 2019

Related U.S. Application Data

(60) Provisional application No. 62/374,986, filed on Aug. 15, 2016.

(51) Int. Cl.
| C07K 16/28 | (2006.01) |
| A61P 25/28 | (2006.01) |
| A61K 9/00 | (2006.01) |
| A61P 37/06 | (2006.01) |
| A61K 39/00 | (2006.01) |

(52) U.S. Cl.
CPC ........ *C07K 16/2887* (2013.01); *A61K 9/0019* (2013.01); *A61P 25/28* (2018.01); *A61P 37/06* (2018.01); *A61K 2039/505* (2013.01); *A61K 2039/54* (2013.01); *A61K 2039/545* (2013.01); *C07K 2317/21* (2013.01)

(58) Field of Classification Search
CPC .............. C07K 16/2887; A61K 9/0019; A61K 2039/505; A61K 2039/54; A61K 2039/545; A61P 25/28
See application file for complete search history.

(56) References Cited

U.S. PATENT DOCUMENTS

2013/0315901 A1* 11/2013 Derosier ............ C07K 16/2887
424/133.1

FOREIGN PATENT DOCUMENTS

| WO | 2012/096924 | 7/2012 |
| WO | 2013/120012 A2 | 8/2013 |
| WO | 2014/025976 A1 | 2/2014 |
| WO | 2016123329 | 8/2016 |

OTHER PUBLICATIONS

Anonymous: "Genmab Announces Phase III Studies of Ofatumumab in Relapsing Multiple", Jun. 2, 2016 (Jun. 2, 2016) pp. 1-2, XP055422006.
Bar-Or et al., "The MIRROR Study: A Randomized, Double-Blind, Placebo-Controlled, Parallel-Group, Dose-Ranging Study to Investigate the Safety and MRI Efficacy of Subcutaneous Ofatumumab in Subjects with Relapsing-Remitting Multiple Sclerosis (RRMS) (S23.006)", Neurology, vol. 82, Apr. 8, 2014 (Apr. 8, 2014), p. S23.006, XP055422339.
Bar-Or et al., "The MIRROR Study: Treatment Phase Results for a Dose-Ranging Study of Ofatumumab in Subjects With Relapsing—Remitting Multiple Sclerosis", Apr. 29, 2014 (Apr. 29, 2014), XP055422304.
Per Soelberg Sorensen et al., "Safety and efficacy of ofatumumab in relapsing-remitting multiple sclerosis; A phase 2 study", Neurology, vol. 82, Jan. 22, 2014 (Jan. 22, 2014), pp. 573-581, XP055422042.
Per Soelberg Sorensen et al., "Magnetic resonance imaging (MRI) efficacy of ofatumumab in relapsing-remitting multiple sclerosis (RRMS)—24-week results of a phase II study", 26th Congress of the European Committee for Treatment and Research in Multiple Sclerosis (ECTRIMS) & 15th Annual Conference of Rehabilitation in MS (RIMS) Oct. 13, 2010-Oct. 16, 2010, Oct. 16, 2010 (Oct. 16, 2010), XP055191485.
Milo, Ron, "Therapeutic strategies targeting B-cells in multiple sclerosis", Autoimmunity Reviews, Elsevier, Amsterdam, NL, vol. 15, No. 7, Mar. 9, 2016 (Mar. 9, 2016), pp. 714-718, XP029541469.
Farber et al., "Novel Agents for Relapsing Forms of Multiple Sclerosis", Annual Review of Medicine : Selected Topics in the Clinicalsciences, vol. 67, No. , Sep. 17, 2015 (Sep. 17, 2015), pp. 309-321, XP055422052.
Kurrasch, R. et al., "Subcutaneously Administered Ofaturnumab in Rheumatoid Arthritis: A Phase I/II Study of Safety, Tolerability, Pharmacokinetics, and Pharmacodynamics", The Journal of Rheumatology, vol. 40, No. 1, Jun. 1, 2013 (Jun. 1, 2013), pp. 1089-1096, XP055189667.
Hauser, et al., "B-Cell Depletion with Rituximab in Relapsing-Remitting Multiple Sclerosis", The New England Journal of Medicine, Feb. 14, 2008, vol. 358, No. 7, pp. 676-688.
Polman, et al., "A Randomized, Placebo-Controlled Trial of Natalizumab for Relapsing Multiple Sclerosis", The New England Journal of Medicine, Mar. 2, 2006, vol. 354, No. 9, pp. 899-910.
Rudick, et al., "Natalizumab Plus Interferon Beta-1a for Relapsing Multiple Sclerosis", The New England Journal of Medicine, Mar. 2, 2006, vol. 354., No. 9, pp. 911-923.
Kappos, et al., "A Placebo-Controlled Trial of Oral Fingolimod in Relapsing Multiple Sclerosis", The New England Journal of Medicine, Feb. 4, 2010, vol. 362, No. 5, pp. 387-401.

(Continued)

*Primary Examiner* — Sharon X Wen
(74) *Attorney, Agent, or Firm* — Yichen Liu

(57) ABSTRACT

The disclosure is directed to treatment regimens for treating Multiple Sclerosis (MS). These methods utilize administration of ofatumumab, an anti-CD20 monoclonal antibody, to the patient during a loading dose regimen and a maintenance regimen.

18 Claims, 5 Drawing Sheets

(56) References Cited

OTHER PUBLICATIONS

Cohen, et al., "Oral Fingolimod or Intramuscular Interferon for Relapsing Multiple Sclerosis", The New England Journal of Medicine, Feb. 4, 2010, vol. 362, No. 5, pp. 402-415.
Archelos, et al., "The Role of B Cells and Autoantibodies in Multiple Sclerosis", Annals of Neurology, Jun. 2000, vol. 47, No. 6, pp. 694-706.
Frohman, et al., "Multiple Sclerosis—The Plaque and Its Pathogenesis", The New England Journal of Medicine, Mar. 2, 2006, vol. 354, No. 9, pp. 942-955.
McFarland, "The B-cell—Old Player, New Position on the Team", The New England Journal of Medicine, Feb. 14, 2008, vol. 358., No. 7, pp. 664-665.
Bouaziz, et al., "Therapeutic B-cell depletion impairs adaptive and autoreactive CD4+ T-cell activation in mice", The National Academy of Sciences of the USA, Dec. 26, 2007, vol. 104, No. 52, pp. 20878-20883.
Lund, "Cytokine-producing B lymphocytes—key regulators of immunity", CurrOpin Immunol., Jun. 2008, vol. 20, No. 3, pp. 332-338.
Lehmann-Horn, et al., "Targeting B-cells in the treatment of multiple sclerosis: recent advances and remaining challenges". Therapeutic Advances in Neurological Disorders, 2013, vol. 6, No. 3, pp. 161-173.
Kappos, et al., "Ocrelizumab in relapsing-remitting multiple sclerosis: a phase 2, randomised, placebo-controlled, mutlicentre trial", Lancet, 2011, vol. 378, pp. 1779-1787.
Hauser, et al., "Efficacy and safety of ocrelizumab in relapsing multiple sclerosis—results of the interferon-beta-1a-controlled, double-blind, Phase III Opera I and II studies", https://onlinelibrary.ectrims-congress.eu/ectrims/2015/31st/116634/stephen.hauser.efficacy.and.safety.of.ocrelizumab.in.relapsing.multiple.html, A116634;246, Oct. 9, 2015, Retrieved from Internet Feb. 15, 2021, 3 pages.
Hauser, et al., "Ocrelizumab versus Interferon Beta-1a in Relapsing Multiple Sclerosis", The New England Journal of Medicine, Jan. 19, 2017, vol. 376, No. 3, pp. 221-234.
Arzerra® US prescribing information (2016); http://www.accessdata.fda.gov/drugsatfda_docs/label/2016/125326s062lbl.pdf, Jan. 2016, 17 pages.
Sorensen, et al., "Safety and efficacy of ofatumumab in relapsing-remitting multiple sclerosis, A phase 2 study", Neurology, Feb. 18, 2014, vol. 82, pp. 573-581.
Bar-Or, et al., "Subcutaneous ofatumumab in patients with relapsing-remitting multiple Sclerosis", Neurology, May 15, 2018, vol. 90, No. 20 pp. e1805-e1814.
von Büdingen, et al., "B cell exchange across the blood-brain barrier in multiple sclerosis", The Journal of Clinical Investigation, Dec. 2012, vol. 122, No. 12, pp. 4533-4543.
Bleeker, et al., "Estimation of dose requirements for sustained in vivo activity of a therapeutic human anti-CD20 antibody", British Journal of Haematology, Epublished Nov. 28, 2007, vol. 140, No. 3, pp. 303-312.
Lublin, et al., "Defining the clinical course of multiple sclerosis", Neurology, Jul. 15, 2014, vol. 83, pp. 278-286.
Sormani, et al., "Magnetic Resonance Imaging as a Potential Surrogate for Relapses in Multiple Sclerosis: a Meta-analytic Approach", Annals of Neurology, Mar. 2009, vol. 65, No. 3, pp. 268-275.
Sormani, et al., "MRI lesions as a surrogate for relapses in multiple sclerosis: a meta-analysis of randomised trials", Lancet Neurol, 2013, vol. 12, pp. 669-676.

\* cited by examiner

Figure 3

| Loading doses | Target | Simulated % of patients attaining target |
|---|---|---|
| One 20mg dose | 8 cells/µL | 23% |
| Two 20mg doses | | 78% |
| Three 20mg doses | | 97% |
| Four 20mg doses (i.e., 3x20mg loading + first 20mg maintenance dose) | | 99% |
| 60mg loading + first 20mg maintenance dose | | 86% |

Figure 4

| Maintenance Dose | Variability | Est. % additional change over 4wks |
|---|---|---|
| 3mg | Average case | - 51% |
| 10mg | | - 65% |
| 20mg | | - 72% |
| 30mg | | - 75% |
| 60mg | | - 80% |

| Maintenance Dose | Variability | Est. % additional change over 4wks |
|---|---|---|
| 3mg | Worst 5% | +67% |
| 10mg | | +17% |
| 20mg | | - 5% |
| 30mg | | -16% |
| 60mg | | -31% |

REGIMENS AND METHODS OF TREATING MULTIPLE SCLEROSIS USING OFATUMUMAB

TECHNICAL FIELD

The disclosure is directed to a dosing regimen for the anti-CD20 monoclonal antibody ofatumumab, to treat Multiple Sclerosis (MS). The dosing regimen uses lower doses than have been used previously with other anti-CD20 monoclonal antibodies, which allows for subcutaneous administration of ofatumumab. The dosing regimen also uses a loading dose regimen followed by a maintenance dose regimen.

BACKGROUND OF THE DISCLOSURE

Multiple Sclerosis (MS) is a chronic, immune-mediated disease of the central nervous system characterized by inflammation, demyelination and axonal/neuronal destruction, ultimately leading to severe disability Standard of care first-line therapies include injectable compounds with modest efficacy, good safety profile and well known tolerability issues (interferon-beta and glatiramer acetate). More efficacious drugs for treating MS are natalizumab and fingolimod. Natalizumab is a monoclonal antibody (mAb) directed against alpha-4 integrins on lymphocytes and has shown efficacy in RMS patients (Polman et al. (2006); Rudick et al. (2006)). However, natalizumab is predominantly restricted to use as a second-line therapy due to the risk of a fatal opportunistic infection (i.e. progressive multifocal leukoencephalopathy or PML). Fingolimod is an oral S1P receptor modulator that has also shown efficacy in relapsing MS and is approved as either first-line (e.g., US) or second-line (e.g., EU) therapy. Fingolimod has shown efficacy both compared to placebo and to one of the current first-line therapies, interferon beta-1a IM (Kappos et al. (2010); Cohen et al. (2010)). Fingolimod is associated with well-known S1P-related safety risks (e.g. bradyarrhythmias upon treatment initiation that require first-dose monitoring), macular edema, hypertension and liver transaminase elevations.

Given that highly efficacious drugs for the treatment of MS have associated risks, while first-line therapies have only modest efficacy, there remains a need to identify pharmaceuticals and accompanying dosing regimens that provide high efficacy with a safety profile comparable to, or better than, that of first line therapies.

BRIEF SUMMARY OF THE DISCLOSURE

The present invention provides a method of treating, arresting or preventing Multiple Sclerosis (MS) with the anti-CD20 antibody ofatumumab or a antigen binding fragment thereof in a patient suffering therefrom, comprising administering to the patient at least one subcuraneous dose of ofatumumab or an antibody fragment thereof.

Disclosed herein are methods of treating MS, comprising a) administering ofatumumab or antigen binding fragment thereof to a patient in need thereof during a loading dose regimen, wherein the loading dose regimen comprises administering the patient a loading dose of ofatumumab at least once prior to administration of a first maintenance dose; and b) thereafter administering ofatumumab or an antigen binding fragment thereof to the patient during a maintenance regimen, wherein the maintenance regimen comprises administering the patient about 3 mg to about 60 mg ofatumumab or antigen binding fragment thereof at week 4 and every four weeks thereafter.

Disclosed herein are methods of treating MS, comprising a) administering ofatumumab or antigen binding fragment thereof to a patient in need thereof during a loading dose regimen, wherein the loading dose regimen comprises administering the patient a loading dose of ofatumumab at least once prior to administration of a first maintenance dose; and b) thereafter administering ofatumumab or an antigen binding fragment thereof to the patient during a maintenance regimen, wherein the maintenance regimen comprises administering the patient about 3 mg, 10 mg, 20 mg, 30 mg, or 60 mg ofatumumab or antigen binding fragment thereof at week 4 and every four weeks thereafter.

Disclosed herein are methods of treating MS, comprising a) administering ofatumumab or antigen binding fragment thereof to a patient in need thereof during a loading dose regimen, wherein the loading dose regimen comprises administering the patient a loading dose of ofatumumab at least three times prior to administration of a first maintenance dose; and b) thereafter administering ofatumumab or an antigen binding fragment thereof to the patient during a maintenance regimen, wherein the maintenance regimen comprises administering the patient about 3 mg, 10 mg, 20 mg, 30 mg, or 60 mg ofatumumab or antigen binding fragment thereof at week 4 and every four weeks thereafter.

Disclosed herein are methods of treating MS, comprising
  a) administering ofatumumab or antigen binding fragment thereof to a patient in need thereof during a loading dose regimen, wherein the loading dose regimen comprises administering the patient 3-60 mg, or about 3 mg, or about 10 mg, or about 20 mg, or about 30 mg, or about 60 mg, ofatumumab at day 0, day 7 and day 14, prior to administration of a first maintenance dose. Preferably, the loading dose is 20 mg ofatumumab; and
  b) thereafter administering ofatumumab or an antigen binding fragment thereof to the patient during a maintenance regimen, wherein the maintenance regimen comprises administering the patient about 3 mg, or about 10 mg, or about 20 mg, or about 30 mg, or about 60 mg ofatumumab or antigen binding fragment thereof at week 4 and every four weeks thereafter. Preferably, the maintenance dose is 20 mg ofatumumab.

Disclosed herein are methods of treating MS, comprising a) administering ofatumumab or antigen binding fragment thereof to a patient in need thereof during a loading dose regimen, wherein the loading dose regimen comprises administering the patient 20 mg ofatumumab at day 0, day 7 and day 14, prior to administration of a first maintenance dose; and b) thereafter administering ofatumumab or an antigen binding fragment thereof to the patient during a maintenance regimen, wherein the maintenance regimen comprises administering the patient about 20 mg ofatumumab or antigen binding fragment thereof at week 4 and every four weeks thereafter.

BRIEF DESCRIPTION OF THE DRAWINGS

FIG. 3 shows the results of modeling studies predicting CD19 cell depletion versus loading dose regimen.

FIG. 4 shows the results of modeling studies predicting CD19 cell depletion versus maintenance dosage.

DETAILED DESCRIPTION OF THE DISCLOSURE

Figure 1:
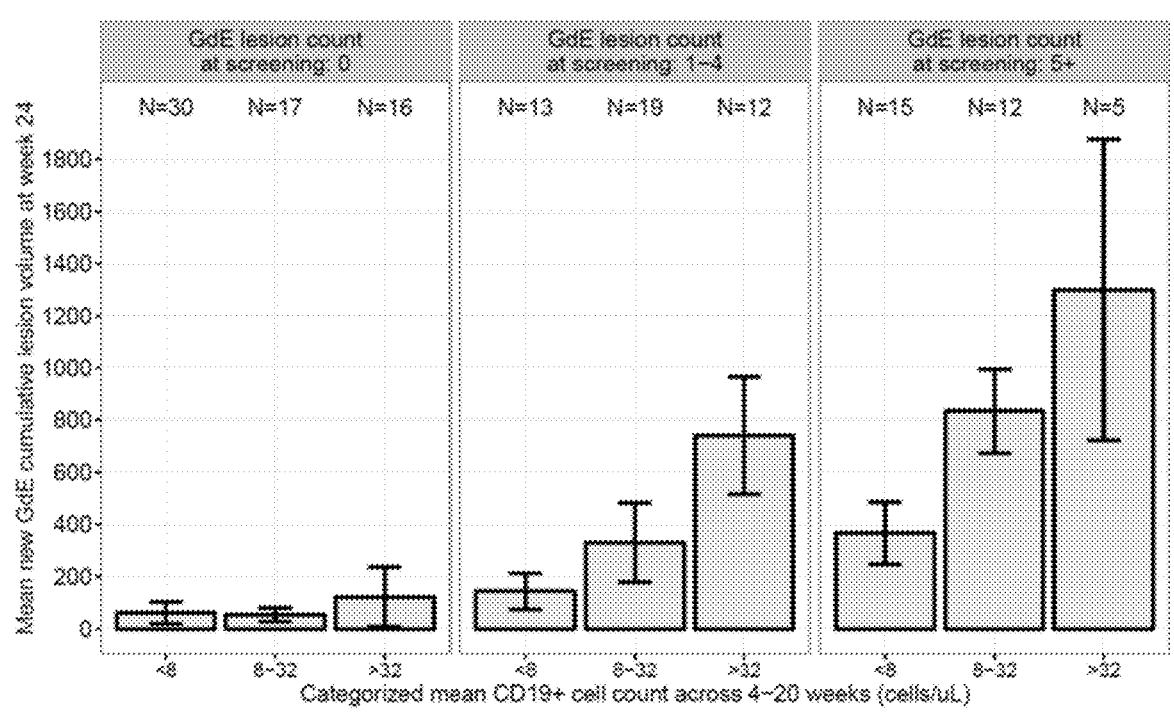
FIG. 1 shows the mean cumulative new GdE lesion volume at week 24 by number of GdE lesions at baseline and average CD19 B cell Count categories across 4-20 weeks.

Multiple Sclerosis (MS) is a chronic, immune-mediated disease of the central nervous system (CNS) characterized by inflammation, demyelination and axonal/neuronal destruction, ultimately leading to severe disability.

There is accumulating evidence that the immune-mediated damage in MS involves more than just T cells. Specifically, the early role of B-cells in the contribution to the immune-mediated histopathology in MS (Archelos et al. 2000; Frohman et al. 2006; McFarland 2008), has become clearer. B-cells have essential functions in regulating immune response and may contribute to disease pathogenesis by self-antigen presentation, serving as cellular adjuvants for CD4+ T-cell activation (Bouaziz et al. 2007) and by regulating T-cell function and inflammation via cytokine production (Lund 2008), in addition to producing autoantibodies. B-cells are present in the chronic plaques, areas of demyelination, and in the cerebrospinal fluid of MS patients (Klaus et al. 2013).

Clinical evidence from the Phase 2 studies with rituximab (Hauser et al. 2008) and ocrelizumab (Kappos et al. 2011) showed B-cell depletion by these agents lead to marked reductions in MRI-measured inflammatory activity in relapsing MS patients. Recently the efficacy of ocrelizumab was confirmed in 2 Phase 3 trials in patients with RMS (Hauser et al. 2015; Hauser et al., 2017). These studies showed that ocrelizumab significantly reduced relapse rates, reduced MRI disease activity and, delayed the time to disability worsening vs interferon beta 1a over 2 years.

There may be problems associated with the use of anti-CD20 monoclonal antibodies such as Rituximab and Ocrelizumab to treat MS. First, rituximab is a chimeric antibody, and chimeric antibodies are more immunogenic than their humanized (ocrelizumab) and fully human (ofatumumab) counterparts. In addition, high dose regimens, such as those used with rituximab and ocrelizumab, lead to profound depletion of B-cells in many compartments. This in turn can result in a higher incidence of infection, and a coincident loss of effective management of B-cell effects, than would a regimen employing doses of an anti-CD20 monoclonal antibody that give a more precise and reversible B-cell depletion. In addition, high doses of rituximab and ocrelizumab are administered as intravenous infusions, which must be administered in a clinic by a healthcare professional, and which can lead to a high incidence of infusion reactions (Hauser et al. 2008; Hauser et al., 2015). Given the downside of using "cancer-like" high dose B cell depletion regimens to treat MS, it would be beneficial to find a more convenient and safer regimen to treat MS with anti-CD20 monoclonal antibodies, with equal or better efficacy.

Accordingly, there is still unmet need for an advanced treatment targeting B-cell pathology with a similar mechanism of action with high efficacy, an acceptable safety profile and the convenience of self-administration.

Ofatumumab is a human anti-CD20 monoclonal antibody (mAb) approved for the treatment of patients with chronic lymphocytic leukemia (Arzerra®). The actions of ofatumumab on Bcells are similar to rituximab and ocrelizumab. Ofatumumab recognizes a unique epitope localized close to the cell membrane on the 2 extracellular domains of the CD20+ molecule, N-proximal of the epitope for the anti-CD20 monoclonal antibody (mAb) rituximab. CD20-binding of ofatumumab induces B-cell lysis primarily through complement-dependent cytotoxicity (CDC) and antibody-dependent cell-mediated cytotoxicity (ADCC), and not by apoptosis (unlike Rituximab). As a fully human antibody (Ab), ofatumumab is predicted to have low potential for immunogenicity, as confirmed by the very low incidence of anti-drug antibodies (ADA) against ofatumumab observed in clinical studies (<1% of patients in oncology studies; Arzerra® US prescribing Information, 2016).

Ofatumumab targets a novel epitope on the CD20 molecule distinct from rituximab (RTX), a chimeric anti-CD20 MAb. RTX studies have utilized high intravenous (IV) doses (two 1000 mg doses 14 days apart) leading to very rapid B cell lysis resulting in infusion reactions despite the use of IV corticosteroid (CS) premedication. The first study involving ofatumumab was a phase I/II study to investigate the use of a low dose subcutaneous (SC) formulation of ofatumumab in rheumatoid arthritis (RA), administered without CS, potentially providing more controlled B cell depletion than that seen in the RTX studies. The primary objective was to investigate the safety and tolerability of a single SC dose of ofatumumab in rheumatoid arthritis (RA) patients on background methotrexate (MTX). Secondary objectives included investigating the minimum dose to achieve target peripheral B-cell depletion, the pharmacodynamic dose-response curve and B-cell repletion profile. In this study of RA patients on stable MTX doses, SC ofatumumab doses of 30, 60 or 100 mg resulted in profound and sustained peripheral B-cell depletion. Single doses up to 60 mg were tolerated and may provide a method of achieving B-cell depletion without additional CS premedication. This study established that the duration of peripheral B cell depletion increases with dose of ofatumumab (ofatumumab), an anti-CD20 antibody.

Ofatumumab has also been studied in MS patients. Ofatumumab has been evaluated in 2 Phase 2 studies in patients with RRMS (Studies OMS115102 and OMS112831/MIRROR). Study OMS115102 was a 48-week (24-week crossover), double-blind, placebo-controlled study that evaluated the effects of ofatumumab administered iv in 38 patients with RRMS (Soerensen et al. 2014). The study consisted of 3 dose cohorts (100 mg, 300 mg, 700 mg) with 12 patients randomized in each cohort to ofatumumab or placebo in a 2:1 ratio. After 24 weeks, patients on ofatumumab were switched to placebo and patients on placebo were switched to the ofatumumab dose of their cohort and followed for 24 weeks (Week 24-48). The study showed that iv administration of ofatumumab resulted in a profound reduction in circulating B-cell counts and suppression of MRI lesion activity (up to 96% reduction in lesion activity versus placebo) at each dose level evaluated in both treatment periods (Teeling et al. (2004), Blood 104(6):1793-800).

OMS112831/MIRROR was a phase 2b, 48-week study (24-week double-blind treatment phase, then 24-week follow-up phase) that examined the efficacy and safety of a wide range of repeat-dose subcutaneous ofatumumab in relapsing-remitting multiple sclerosis (RRMS) (Bar-Or, 2016). In this study, called MIRROR (MRI study In RRMS: evaluating ofatumumab Regimen), patients received ofatumumab 3 mg, 30 mg, or 60 mg every 12 weeks (q12w), or ofatumumab 60 mg every 4 weeks (q4w). To evaluate whether tolerability to the higher ofatumumab doses (30 mg and 60 mg) could be improved by the administration of an initial, lower, conditioning dose of ofatumumab (theoretically leading to the gradual lysis of B cells and potentially reducing cytokine release reactions), patients in the 30 mg q12w, 60 mg q12w and 60 mg q4w dose groups were randomized (1:1) to receive either placebo or a conditioning dose of ofatumumab 3 mg at week 0.

The primary endpoint was the cumulative number of new gadolinium-enhancing lesions during weeks 0-12 on brain magnetic resonance imaging (MRI). Other endpoints included
(i) the cumulative number of new Gd-enhancing lesions at other time points;
(ii) (ii) the total volume at weeks 12 and 24 of a) new Gd-enhancing lesions, b) new/newly enlarged T2 lesions, and c) T1 hypointense lesions;
(iii) the proportion of patients free from relapses;
(iv) Expanded Disability Status Scale (EDSS) scores;
(v) Multiple Sclerosis Functional Composite (MSFC) and their component scores;
(vi) Modified Fatigue Impact Scale (MFIS); and
(vii) Evaluation of the use of the initial conditioning ofatumumab dose.

Ofatumumab reduced the mean cumulative number of new gadolinium-enhancing lesions by 65% vs placebo during weeks 0-12 (p<0.001), and by ≥90% during weeks 4-12 vs placebo in a post hoc analysis of cumulative ofatumumab doses ≥30 mg (p<0.001). Ofatumumab reduced cumulative new/newly enlarged T2 lesions vs placebo during weeks 0-12 (60-72%; p≤0.002), and depleted CD19 B-cells dose-dependently. During weeks 0-12, 17/164 patients (10%) receiving ofatumumab experienced a relapse versus 9/67 patients (13%) receiving placebo. Notably, there was no benefit in administering the 3 mg conditioning dose.

Overall, these results shows that ofatumumab SC can suppress new brain MRI lesions at doses considerably lower than previously studied in patients with MS. The results also demonstrated a rapid, dose and dose frequency dependent reduction in B-cell counts, the effect being less pronounced with the 3 mg q12 regimen. Monthly dosing showed no signs of B-cell repletion during the inter-dosing interval. Both 30 mg and 60 mg q12 weeks showed approximately 95% suppression of B-cells in the blood compartment prior to re-dosing. Once dosing was ceased, all treatments showed relatively rapid B-cell repopulation over 60 weeks of follow up as compared to high-dose i.v. anti-CD20 antibodies. Inhibition of CD19+ B cells by treatment group is shown in FIG. 1. Monthly dosing showed no signs of B-cell repletion during the inter-dosing interval, whereas both 30 mg and 60 mg q12 weeks showed approximately 75% suppression of B cells prior to redosing. On a semi-log scale, once dosing has ceased, all treatments showed similar rate of B-cell repopulation, as evidenced by parallel growth curves (FIG. 1). The sustained suppression of new Gd-enhancing and T2 lesions with ofatumumab is consistent with effects demonstrated by other anti-CD20 mAbs at doses resulting in maximal peripheral B-cell depletion (von Budingen et al. 2012; Bleeker et al. 2008).

Overall, ofatumumab was safe and well tolerated in patients with RRMS. The safety profile of ofatumumab was consistent with previous data; no new signals were reported.

In study OMS112831/MIRROR of s.c. ofatumumab, the most commonly reported AEs across the ofatumumab dose groups were injection-related reactions (52% for ofatumumab, 15% for placebo). Injection-related reactions occurred primarily post-first dose, diminished on subsequent dosing and were mostly mild/moderate in severity (97% of the events). There were no notable differences across treatment groups in the overall incidence of infection-related AEs, including urinary and respiratory tract infections. Few serious adverse events (SAEs) were reported. These were mainly systemic injection-related reactions (3 patients), all occurring on Day 1 and in the 60 mg ofatumumab dose groups. There were no cases of opportunistic infections reported during the study.

The term "comprising" encompasses "including" as well as "consisting," e.g. a composition "comprising" X may consist exclusively of X or may include something additional, e.g., X+Y.

The term "about" in relation to a numerical value x means +/−10% unless the context dictates otherwise.

The term "immunoglobulin" as used herein refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See, for instance, Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region, CH, typically is comprised of three domains, CH1, CH2, and CH3. Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases, such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (for instance residue 52a according to Kabat) after residue 52 of VH CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" as used herein refers to an immunoglobulin molecule, a fragment of an immunoglobulin molecule, or a derivative of either thereof, which has the ability to specifically bind to an antigen under typical physiological conditions for a significant period of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or a time sufficient for the antibody to recruit an Fc-mediated effector activity). The term "antigen-binding portion" of an antibody as used herein, refers to fragments of an antibody that retain the ability to specifically bind to an antigen (e.g., CD20). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR.

The variable regions of the heavy and light chains of the immunoglobulin molecule contain a binding domain that interacts with an antigen. The constant regions of the antibodies may mediate the binding of the immunoglobulin to host tissues or factors, including various cells of the immune system (such as effector cells) and components of the complement system such as C1q, the first component in the classical pathway of complement activation.

As indicated above, the term "antibody" as used herein, unless otherwise stated or clearly contradicted by the context, includes fragments of an antibody provided by any known technique, such as enzymatic cleavage, peptide synthesis and recombinant techniques that retain the ability to specifically bind to an antigen. It has been shown that the antigen-binding function of an antibody may be performed by fragments of a full-length (intact) antibody. Examples of antigen-binding fragments encompassed within the term "antibody" include, but are not limited to (i) a Fab fragment, a monovalent fragment consisting of the VL, VH, CL and CH1 domains; (ii) F(ab)2 and F(ab')2 fragments, bivalent fragments comprising two Fab fragments linked by a disulfide bridge at the hinge region; (iii) a Fd fragment consisting essentially of the VH and CH 1 domains; (iv) a Fv fragment consisting essentially of the VL and VH domains of a single arm of an antibody, (v) a dAb fragment (Ward et al., Nature 341, 544-546 (1989)), which consists essentially of a VH domain and also called domain antibodies (Holt et al. (November 2003) Trends Biotechnol. 21 (11):484-90); (vi) a camelid antibody or nanobody (Revets et al. (January 2005) Expert Opin Biol Ther. 5 (1):111-24), (vii) an isolated complementarity determining region (CDR), such as a VH CDR3, (viii) a UniBody™, a monovalent antibody as disclosed in WO 2007/059782, (ix) a single chain antibody or single chain Fv (scFv), see for instance Bird et al., Science 242, 423-426 (1988) and Huston et al., PNAS USA 85, 5879-5883 (1988)), (x) a diabody (a scFv dimer), which can be monospecific or bispecific (see for instance PNAS USA 90(14), 6444-6448 (1993), EP 404097 or WO 93/11161 for a description of diabodies), a triabody or a tetrabody. Although such fragments are generally included within the definition of an antibody, they collectively and each independently are unique features of the present invention, exhibiting different biological properties and utility. These and other useful antibody fragments in the context of the present invention are discussed further herein.

It should be understood that the term antibody generally includes monoclonal antibodies as well as polyclonal antibodies. The antibodies can be human, humanized, chimeric, murine, etc. An antibody as generated can possess any isotype.

The term "human antibody", as used herein, is intended to include antibodies having variable and constant regions derived from human germline immunoglobulin sequences. The human antibodies of the present invention may include amino acid residues not encoded by human germline immunoglobulin sequences (for instance mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted into human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, a human antibody derived from a particular human germline sequence will display no more than 10 amino acid differences, such as no more than 5, for instance no more than 4, 3, 2, or 1 amino acid difference from the amino acid sequence encoded by the germline immunoglobulin gene. For VH antibody sequences the VH CDR3 domain is not included in such comparison.

The term "chimeric antibody" refers to an antibody that contains one or more regions from one antibody and one or more regions from one or more other antibodies. The term "chimeric antibody" includes monovalent, divalent, or polyvalent antibodies. A monovalent chimeric antibody is a dimer (HL)) formed by a chimeric H chain associated through disulfide bridges with a chimeric L chain. A divalent chimeric antibody is a tetramer (H2L2) formed by two HL dimers associated through at least one disulfide bridge. A polyvalent chimeric antibody may also be produced, for example, by employing a CH region that assembles into a molecule with 2+ binding sites (for instance from an IgM H chain, or .mu. chain). Typically, a chimeric antibody refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for instance U.S. Pat. No. 4,816,567; see also Morrison et al., PNAS USA 81, 6851-6855 (1984)). Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO 86/01533, EP184187, Sahagan et al., J. Immunol. 137, 1066-1074 (1986), WO 87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

The term "humanized antibody" refers to a human antibody which contain minimal sequences derived from a non-human antibody. Typically, humanized antibodies are human immunoglobulins (recipient antibody) in which residues from a hypervariable region of the recipient are replaced by residues from a hypervariable region of a non-human species (donor antibody), such as mouse, rat, rabbit or non-human primate having the desired specificity, affinity, and capacity.

Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody optionally also will comprise at least a portion of a human immunoglobulin constant region. For further details, see Jones et al., Nature 321, 522-525 (1986), Riechmann et al., Nature 332, 323-329 (1988) and Presta, Curr. Op. Struct. Biol. 2, 593-596 (1992).

The term "CD19" refers to B-lymphocyte antigen CD19 (CD19=Cluster of Differentiation 19), is a protein that in humans is encoded by the CD19 gene and is found on the surface of B-cells, a type of white blood cell. The term "B cells" refers to a type of white blood cell. B cells are also known as B lymphocytes, They function in the humoral immunity component of the adaptive immune system by secreting antibodies—Additionally, B cells present antigen (they are also classified as professional antigen-presenting cells (APCs)) and secrete cytokines. As used herein, "CD19 cells" and "B cells" refer to the same type of cell.

The term "patient" refers to a human patient.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further elsewhere herein), (b) antibodies isolated from a host cell transformed to express the antibody, such as from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) J. Biol. Chem. 264 (19):11282-11287; and Einfield et al. (1988) EMBO J. 7 (3):711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) Blood 63 (6): 1424-1433), but is not found on hematopoietic stem cells, pro-B cells, normal plasma cells, or other normal tissues (Tedder et al. (1985) J. Immunol. 135 (2):973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class II .alpha. or .beta. chains, which have relatively short intracytoplasmic regions of 3, 3, 28, 15, and 16 amino acids, respectively (Komaromy et al. (1983) NAR 11:6775-6785). Of the last 61 carboxyl-terminal amino acids, 21 are acidic residues, whereas only 2 are basic, indicating that this region has a strong net negative charge. The GenBank Accession No. is NP_690605.

The anti-CD20 antibody ofatumumab of the present invention may be administered via any suitable route, such as an oral, nasal, inhalable, intrabronchial, intraalveolar, topical (including buccal, transdermal and sublingual), rectal, vaginal and/or parenteral route. In one embodiment, a pharmaceutical composition of the present invention is administered subcutaneously (s.c.), typically by injection. In one embodiment, SC administration of the pharmaceutical composition comprising afatumumab is achieved using an autoinjector. A non-limiting example of an autoinjector suitable for use according to the present invention is the Sensoready® pen.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment of the invention, the ofatumab composition is formulated in accordance with routine procedures as a pharmaceutical composition adapted for intravenous administration to human beings. Typically, compositions for intravenous administration are solutions in sterile isotonic aqueous buffer. Where suitable, the composition may also include a solubilizing agent and a local anesthetic, such as lignocaine, to ease pain at the site of the injection. Generally, the ingredients are supplied either separately or mixed together in unit dosage form, for example, as a dry lyophilized powder, or water-free concentrate, in a hermetically sealed container, such as an ampoule or sachette, indicating the quantity of active agent.

Where the composition is to be administered by infusion, it can be dispensed with an infusion bottle containing sterile pharmaceutical grade water or saline.

Where the composition is administered by injection, an ampoule of sterile water for injection or saline can be provided so that the ingredients may be mixed prior to administration.

In one embodiment, a formulation for ofatumuamb can be formulated according to a formulation disclosed in WO/2009/009407.

In one embodiment, ofatumumab is formulated in an antibody formulation wherein ofatumumab is present in an amount of about 20-300 mg/mL, 50-300 mg/mL, 100-300 mg/mL, 150-300 mg/mL, 200-300 mg/mL, or 250-300 mg/mL, preferably at 50 mg/ml.

In one embodiment, ofatumumab is formulated in an antibody formulation wherein the formulation comprises 10 to 100 mM sodium acetate, 25 to 100 mM sodium chloride, 0.5 to 5% arginine free base, 0.02 to 0.2 mM EDTA, 0.01 to 0.2% polysorbate 80, and adjusted to pH 5.0 to 7.0. Preferably the ofatumumab formulation comprises 50 mM sodium acetate, 51 mM sodium chloride, 1% arginine free base, 0.05 mM EDTA, 0.02% polysorbate 80, and adjusted to pH 5.5.

In one embodiment, the ofatumumab formulation is provided in a pre-filled syringe.

In one embodiment, a method of treating Multiple Sclerosis (MS) is provided, comprising a) administering ofatumumab to a patient in need thereof during a loading dose regimen; and b) thereafter administering ofatumumab to the patient during a maintenance regimen.

In one embodiment, a method for alleviating or delaying progression of the symptoms of Multiple Sclerosis is provided, comprising a) administering ofatumumab to a patient in need thereof during a loading dose regimen; and b) thereafter administering ofatumumab to the patient during a maintenance regimen.

In one embodiment, a method for slowing progression of Multiple Sclerosis is provided, comprising a) administering ofatumumab to a patient in need thereof during a loading dose regimen; and b) thereafter administering ofatumumab to the patient during a maintenance regimen.

In one embodiment, the loading dose is between about 15 mg and about 25 mg of ofatumamab, preferably between about 18 mg and about 22 mg ofatumumab, most preferably about 20 mg ofatumumab. In one embodiment, the maintenance dose is between about 15 mg and about 25 mg of ofatumamab, preferably between about 18 mg and about 22 mg ofatumumab, and preferably about 20 mg ofatumumab. In one embodiment, both the loading dose and the maintenance does are between about 15 mg and about 25 mg of ofatumamab, preferably between about 18 mg and about 22 mg ofatumumab, most preferably about 20 mg ofatumumab.

In one embodiment, a method of treating Multiple Sclerosis (MS) is provided, comprising the following regimen: a) ofatumumab is administered to a patient in need thereof during a loading dose regimen comprising s.c. injections of 20 mg ofatumumab at day 0, day 7 and day 14 of the dosage regimen; and b) ofatumumab is administered to a patient in need thereof during a maintenance dose regimen comprising s.c. injections of 20 mg ofatumumab starting at week four of the dosage regimen and continuing thereafter every four weeks for the duration of the treatment protocol.

In one embodiment, a method for alleviating or delaying progression of the symptoms of Multiple Sclerosis (MS) is provided, comprising the following regimen: a) ofatumumab is administered to a patient in need thereof during a loading dose regimen comprising s.c. injections of 20 mg ofatumumab at day 0, day 7 and day 14 of the dosage regimen; and b) ofatumumab is administered to a patient in need thereof during a maintenance dose regimen comprising s.c. injections of 20 mg ofatumumab starting at week four of the dosage regimen and continuing thereafter every four weeks for the duration of the treatment protocol.

In one embodiment, a method for slowing progression of Multiple Sclerosis (MS) is provided, comprising the following regimen: a) ofatumumab is administered to a patient in need thereof during a loading dose regimen comprising s.c. injections of 20 mg ofatumumab at day 0, day 7 and day 14 of the dosage regimen; and b) ofatumumab is administered to a patient in need thereof during a maintenance dose regimen comprising s.c. injections of 20 mg ofatumumab starting at week four of the dosage regimen and continuing thereafter every four weeks for the duration of the treatment protocol.

In one embodiment, ofatumumab for use in a method for treating Multiple Sclerosis (MS) is provided, the method comprising a) administering ofatumumab to a patient in need thereof during a loading dose regimen; and b) thereafter administering ofatumumab to the patient during a maintenance regimen.

In one embodiment, ofatumumab for use in a method for treating Multiple Sclerosis (MS) is provided, the method comprising a) ofatumumab is administered to a patient in need thereof during a loading dose regimen comprising s.c. injections of 20 mg ofatumumab at day 0, day 7 and day 14 of the dosage regimen; and b) ofatumumab is administered to a patient in need thereof during a maintenance dose regimen comprising s.c. injections of 20 mg ofatumumab starting at week four of the dosage regimen and continuing thereafter every four weeks for the duration of the treatment protocol.

In one embodiment, ofatumumab in the manufacture of a medicament for use in a method of treating Multiple Sclerosis (MS) is provided, wherein the method comprises a) administering ofatumumab to a patient in need thereof during a loading dose regimen; and b) thereafter administering ofatumumab to the patient during a maintenance regimen.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. Unless defined otherwise, all technical and scientific terms used herein have the same meaning as commonly understood by one of ordinary skill in the art to which this disclosure belongs. All patents and publications cited in this specification are incorporated by reference. The following Example is presented in order to more fully illustrate the preferred embodiment of the disclosure. This example should in no way be construed as limiting the scope of the disclosed patient matter, as defined by the appended claims.

EXAMPLE

A Randomized, Double-Blind, Double-Dummy, Parallel-Group Study Comparing the Efficacy and Safety of Ofatumumab Versus Teriflunomide in Patients with Relapsing Multiple Sclerosis The study is designed, in conjunction with a second study of identical design conducted in parallel, to provide efficacy, safety and tolerability data for ofatumumab s.c. compared to oral teriflunomide (Aubagio®) in patients with relapsing MS.

The primary objective of this study is to demonstrate that ofatumumab 20 mg subcutaneous (s.c.) once every 4 (q4) weeks is superior to teriflunomide 14 mg oral once daily in reducing the frequency of confirmed relapses as evaluated by the annualized relapse rate (ARR) in patients with relapsing MS.

Secondary objectives include (i) time to disability worsening as measured by 3-month confirmed worsening (3mCDW) on the Expanded Disability Status Scale (EDSS); (ii) time to disability worsening as measured by 6-month confirmed worsening (6mCDW) on EDSS; (iii) time to disability improvement as measured by 6-month confirmed improvement (6mCDI) on EDSS; (iv) number of T1 Gd-enhancing lesions per MRI scan; (v) number of new or enlarging T2 lesions on MRI per year (annualized T2 lesion rate); and (vi) rate of brain volume loss (BVL) based on assessments of percentage brain volume change from baseline.

Also evaluated are the safety and tolerability of ofatumumab 20 mg s.c. q4 weeks compared to teriflunomide 14 mg p.o. once daily.

Study Design

This is a randomized, double-blind, double-dummy, active comparator-controlled, parallel group, multi-center study with variable treatment duration, in patients with relapsing MS. Eligible patients will be randomized to receive either ofatumumab 20 mg s.c. injections q4 weeks (after initial loading regimen of three weekly 20 mg doses in the first 14 days) or teriflunomide 14 mg orally once daily. In order to blind for the different formulations, a double-dummy design will be used: patients in the active ofatumumab treatment arm will additionally take placebo capsules orally once daily; patients in the active teriflunomide treatment arm will additionally take q4 weeks placebo-containing s.c. injections (after initial regimen of three weekly injections in the first 14 days).

Patients with relapsing MS (RRMS or SPMS with disease activity as defined by Lublin et al. 2014) with EDSS scores of 0 to 5.5 will be enrolled. Specific disease activity criteria define a population with active inflammatory disease based on recent relapse in the one or 2 years before enrollment or one or more Gd-enhancing lesions on MRI in the year prior to randomization. The defined trial population is typical for relapsing MS.

Loading Dose Regimen and Maintenance Dose Regimen

The dose regimen for ofatumumab for this study is a loading dose regimen of 20 mg at Day 1, Day 7 and Day 14, followed by a monthly maintenance dose regimen of 20 mg administered every 4 weeks starting at week 4. The dose selection relies on the clinical hypothesis that the depletion of B-cells in lymphatic tissues is key for efficacy (as measured by MRI and relapses), and that the depletion of brain parenchymal and meningeal B-cells may be an additional factor for the mode of action; blood B-cell count is an imperfect, epiphenomenal measure of tissue status. This hypothesis suggests that in order to attain the desired efficacy, 2 conditions should be met:

a loading dose regimen with high enough initial PK for lymphatic depletion, and a continued maintenance dose that would keep B-cell depletion levels below desired threshold.

The Phase 2 study of ofatumumab s.c. in relapsing MS patients (Study OMS112831/MIRROR) provided important information regarding the relationship between peripheral B-cell depletion and efficacy as measured by MRI Gd-enhancing brain lesions. In that study, a clear dose-response relationship was detected using a quasi-Poisson regression model that related new Gd-enhancing lesion volumes, baseline lesion number and treatment group. The dose-response was fully explained by the extent of the CD19+ cell count drop. The model indicates that lower CD19+ cells levels lead to better control of lesion volumes and, subsequently, high level of depletion of CD19+ cells (e.g. ≤8 cells/µL) should be maintained throughout the treatment course in order to ensure desired efficacy.

Modeling Studies

Figure 2:
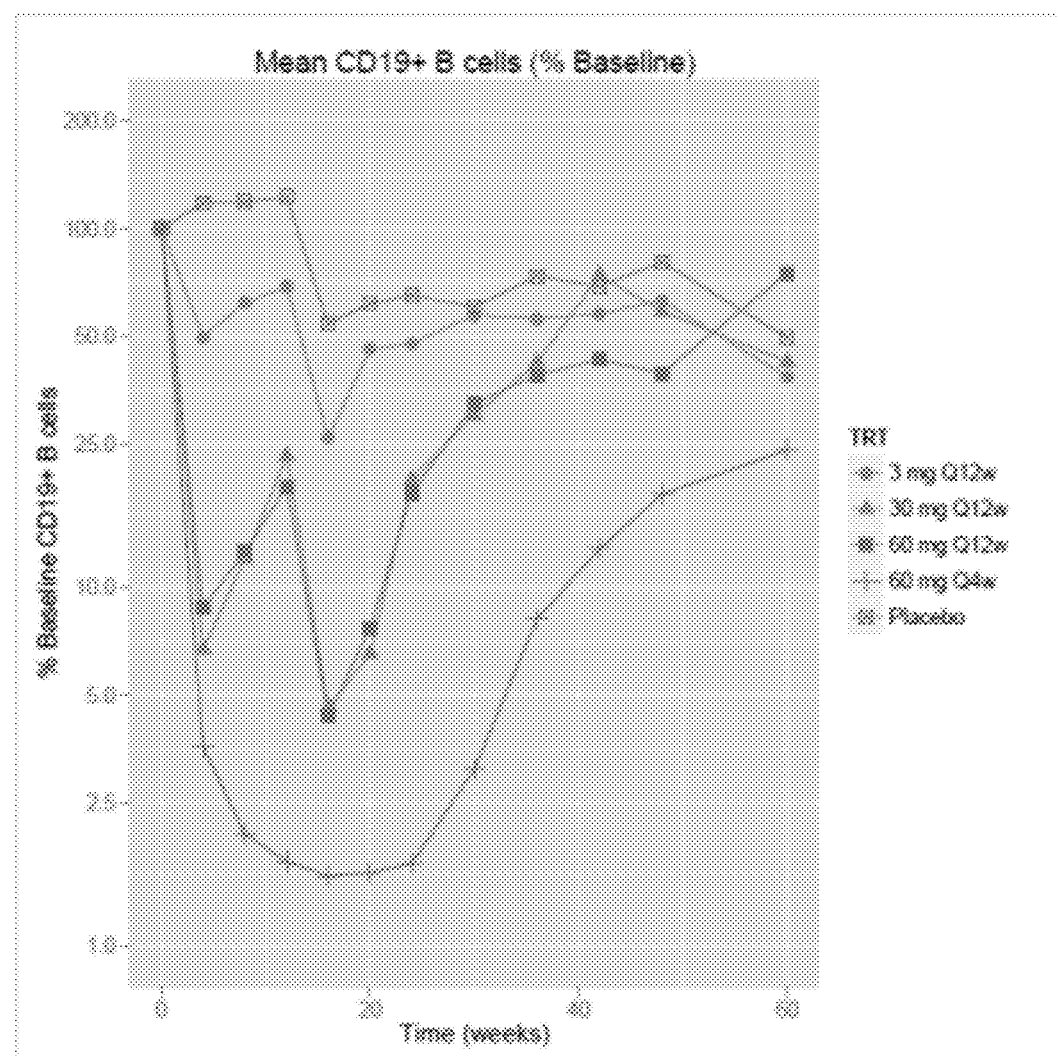
FIG. 2 shows the mean CD19 B Cell Count expressed as percentage of baseline (Semi-log scale) (ITT Population).

It is desirable to achieve maximal MRI efficacy and B-cell depletion below 8 cells/µL without any delay (FIG. 1). Exploratory modeling based on the Phase 2 data of study OMS112831/MIRROR suggested that a single dose of ofatumumab 20 mg s.c. is insufficient to reduce B-cell levels to ≤8 cells/µL (see FIG. 2). As can also be seen in FIGS. 3 and 4, modeling studies predict a high degree of target depletion can be attained via 20 mg administration of ofatumumab with multiple loading doses, and that subsequent maintenance doses (also 20 mg) will either maintain or increase the initial depletion. More specifically, we determined that a loading dose regimen of 3 separate 20 mg doses (at weeks 0, 1 and 2) is required to attain target depletion (≤8 cells/µL) in >95% of patients based on modeling, and is extrapolated to be more effective than a single 60 mg load. Therefore, this loading dose regimen was chosen.

Figure 5:
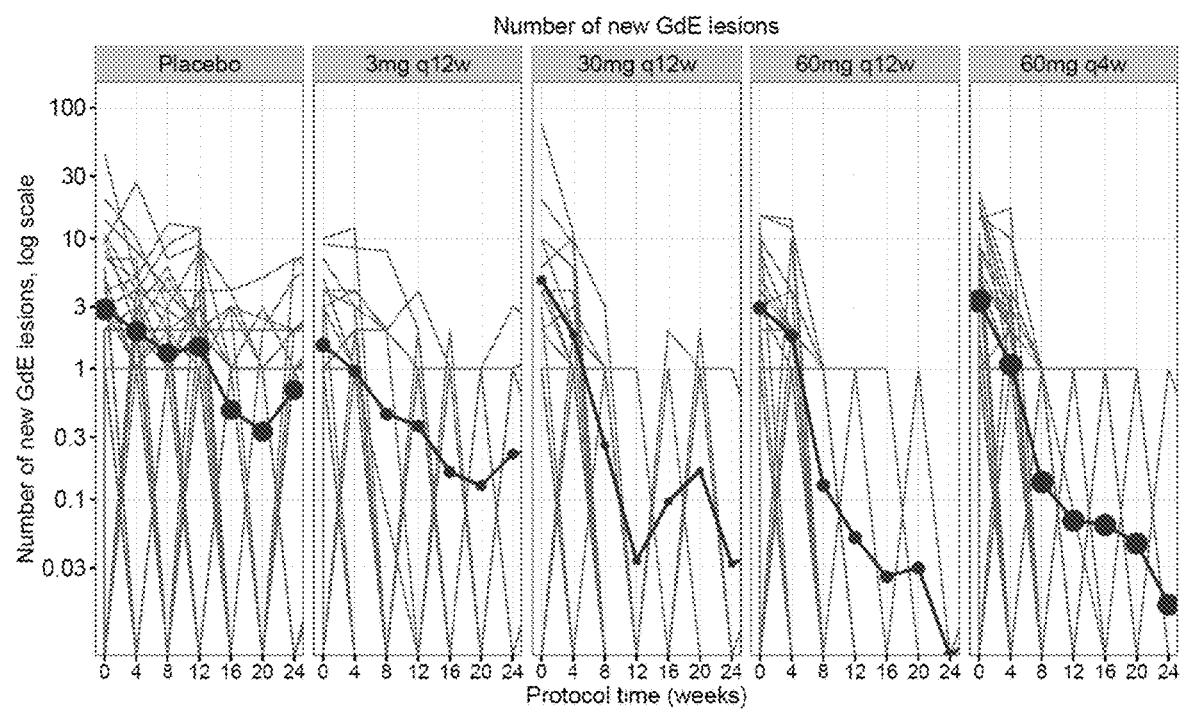
FIG. 5 shows the time course of number of new GdE lesions by treatment arm.

In study OMS112831/MIRROR, ofatumumab administration at 3 mg every 12 weeks, 30 mg every 12 weeks, 60 mg every 12 weeks and 60 mg every 4 weeks were studied. Although 3 mg had a clear MRI effect, and 30 mg every 12 weeks seemed to be very close to maximal MRI efficacy, 60 mg every 12 weeks was also studied to make sure that the maximal MRI effect would really translate to maximal clinical effects on relapses and disability. The highest dose level, 60 mg every 4 weeks, didn't add any efficacy compared with 60 mg every 12 weeks (FIG. 5). However, when B-cell repletion was looked at, we noted that there was a tendency toward B-cell repletion before the next 12 week dose was administered. Because patients dosed with 60 mg q4 weeks showed no signs of B-cell repletion during the inter-dosing interval, we decided on a maintenance dosing inter-dosing interval of 4 weeks (once every 4 (q4) weeks). Modeling studies estimated the rate of B cell repletion vs. dose amount and dosing frequency. MS patient B-cell repletion rates were estimated from the MIRROR study data. The modeling studies showed that for average cases of MS, a 3 mg maintenance dose was deemed adequate at maintaining B-cell depletion over a 4-week period (see FIG. 4, top panel). However, the same modeling estimated that for patients with very high repletion rates (corresponding to the 95$^{th}$ percentile as estimated from the MIRROR study), i.e., in "worst case scenarios", neither 3 mg nor 10 mg maintenance would be adequate to maintain B-cell depletion over a 4-week interval, while 20 mg or higher doses would maintain adequate depletion (see FIG. 4, bottom panel). Thus, based on exploratory modeling, 20 mg ofatumumab appears to be sufficient to either maintain or to further deplete B-cells in >95% of patients who have previously depleted, even in patients with high repletion rates. Therefore, to ensure continued efficacy in maintenance, the inventors decided to split the tested MIRROR dose regimen (60 mg every 12 weeks), to go to 20 mg every 4 weeks.

In study OMS112831/MIRROR, with regards to safety and tolerability, the dose regimens of 60 mg q12 and q4 weeks were associated with more adverse events (AEs) than the lower dose regimens of 3 or 30 mg q12 weeks. In particular, post injection systemic reactions reported as SAEs on Day 1 were seen only with the 60 mg dose regimens. In the presence of B-cells at first dosing, and when B-cells have started repleting, systemic reactions are an expected AE and their severity is likely to be dose and B-cell count related.

Since relapsing MS is a chronic disease with anticipated long-term treatment, dose selection should therefore aim to balance efficacy and safety aspects. The ofatumumab subcutaneous loading dose regimen of 20 mg at Day 1, Day 7 and Day 14, followed by a monthly maintenance dose regimen of 20 mg administered every 4 weeks (starting at week 4) is selected because it will deplete and subsequently maintain B-cells at the levels below 8 cells/µL for nearly all patients and it is expected to have maximal clinical benefit and better tolerability than higher doses. Taken together, the strong relationship between MRI lesions and relapses (Sormani et al. 2009; Sormani et al. 2013) and the observed inhibition of lesions at the cumulative doses tested, combined with maintaining B-cells below threshold support selection of the proposed dose regimen.

REFERENCES CITED HEREIN

1. Hauser et al., B-cell Depletion with Rituximab in Relapsing-Remitting Multiple Sclerosis, *N Engl J Med* 2008; 358:676-88.
2. Polman et al., A Randomized, Placebo-Controlled Trial of Natalizumab for Relapsing Multiple Sclerosis, *N Engl J Med* 2006; 354:899-910.
3. Rudick et al., Natalizumab plus Interferon Beta-1a for Relapsing Multiple Sclerosis, *N Engl J Med* 2006; 354: 911-923.
4. Kappos et al., A Placebo-Controlled Trial of Oral Fingolimod in Relapsing Multiple Sclerosis, *N Engl J Med* 2010; 362:387-401.
5. Cohen et al., Oral Fingolimod or Intramuscular Interferon for Relapsing Multiple Sclerosis, *N Engl J Med* 2010; 362:402-415.
6. Archelos et al., The role of B-cells and autoantibodies in multiple sclerosis, *Ann Neurol* 2000; 47:694-706.
7. Frohman et al., Multiple sclerosis—the plaque and its Pathogenesis, *New Engl J Med* 2006; 354:942-955.
8. McFarland, The B-cell—old player, new position on the team, *N Engl J Med* 2008; 358:664-5.
9. Bouaziz et al., Therapeutic B-cell depletion impairs adaptive and autoreactive CD4+ T-cell activation in mice, *Pro. Natl. Acad. Sci. USA* 2007; 104:20882-20887.
10. Lund, Cytokine-producing B lymphocytes—key regulators of immunity, *Curr Opin Immunol.* 2008; 20 (3): 332-38.
11. Klaus Lehmann-Horn et al., Targeting B-cells in the Treatment of Multiple Sclerosis, *Ther Adv Neurol Disorders* 2013; 6 (3):161-173.
12. Kappos et al., Ocrelizumab in relapsing-remitting multiple sclerosis: a Phase 2, randomized, placebo-controlled, multicentre trial, *Lancet* 2011; 378:1779-87.
13. Hauser et al., Efficacy and safety of ocrelizumab in relapsing multiple sclerosis—results of the interferon-beta-1a-controlled, double-blind, Phase III OPERA I and II studies, *ECTRIMS Online Library*; Hauser, 2015; 116634.
14. Hauser et al., Ocrelizumab versus Interferon Beta-1a in Relapsing Multiple Sclerosis, *N Engl J Med* 2017; 376 (3):221-234.
15. Arzerra® US prescribing information (2016); http://www.accessdata.fda.gov/drugsatfda_docs/label/2016/125326s062lbl.pdf.
16. Soerensen et al., Safety and efficacy of ofatumumab in relapsing remitting multiple sclerosis, *Neurology* 2014; 82:573-581.
17. Bar-Or et al., Subcutaneous ofatumumab in patients with relapsing-remitting multiple Sclerosis, 2016 (manuscript in preparation).
18. von Budingen et al., B cell exchange across the blood-brain barrier in multiple sclerosis, *The Journal of Clinical investigation* 2012; 122 (12):4533-43.
19. Bleeker et al., Estimation of dose requirements for sustained in vivo activity of a therapeutic human anti-CD20 antibody, *British Journal of Haematology* 2008 (Epub Nov. 27, 2007); 140 (3):303-12.
20. Lublin et al., Defining the clinical course of multiple sclerosis, *Neurology* 2014; 83:278-286.
21. Sormani et al., Magnetic resonance imaging as a potential surrogate for relapses in multiple sclerosis: a metaanalytic approach, *Ann Neurol.* 2009; 65 (3):268-75.
22. Sormani et al., MRI lesions as a surrogate for relapses in multiple sclerosis: a meta-analysis of randomised trials, *Lancet Neurol* 2013; 12: 669-676.

What is claimed is:

1. A method of treating Multiple Sclerosis (MS), comprising a) administering ofatumumab to a patient in need thereof during a loading dose regimen comprising administering 20 mg ofatumumab at weeks 0, 1 and 2; and b) thereafter administering ofatumumab to the patient during a maintenance dose regimen comprising administering 20 mg ofatumumab monthly starting at week 4.

2. The method according to claim 1, wherein ofatumumab is administered by subcutaneous (s.c.) injection during the loading dose regimen and during the maintenance dose regimen.

3. A method of treating Multiple Sclerosis (MS) comprising administering ofatumumab to a patient in need thereof during a loading dose regimen and subsequently a maintenance dose regimen, wherein
    a) ofatumumab is administered to a patient in need thereof during a loading dose regimen comprising administering 20 mg ofatumumab at day 0, day 7 and day 14 of the dosage regimen; and
    b) ofatumumab is administered to a patient in need thereof during a maintenance dose regimen comprising administering 20 mg ofatumumab starting at week four of the dosage regimen and continuing thereafter every four weeks for the duration of the treatment protocol.

4. The method according to claim 3, wherein
    a) ofatumumab is administered to a patient in need thereof during a loading dose regimen comprising s.c. injections of 20 mg ofatumumab at day 0, day 7 and day 14 of the dosage regimen; and b) ofatumumab is administered to a patient in need thereof during a maintenance dose regimen comprising s.c. injections of 20 mg ofatumumab starting at week four of the dosage regimen and continuing thereafter every four weeks for the duration of the treatment protocol.

5. The method according to claim 4 in which 20 mg ofatumumab is administered during the loading dose regimen and the maintenance dose regimen by using an autoinjector loaded with a formulation containing ofatumumab at a concentration of 50 mg/ml.

6. The method according to claim 4 in which 20 mg ofatumumab is administered during the loading dose regimen and the maintenance dose regimen by using a pre-filled syringe filled with a formulation containing ofatumumab at a concentration of 50 mg/ml.

7. The method according to claim 1 in which multiple sclerosis is relapse-remitting multiple sclerosis (RRMS).

8. The method according to claim 1 in which multiple sclerosis is primary progressive multiple sclerosis (PPMS).

9. The method according to claim 1 in which multiple sclerosis is secondary progressive multiple sclerosis (SPMS).

10. The method according to claim 1, wherein the 20 mg ofatumumab is administered during the loading dose regimen and the maintenance dose regimen by using an autoinjector loaded with a formulation containing ofatumumab at a concentration of 20-300 mg/ml.

11. The method according to claim 1, wherein ofatumumab is administered during the loading dose regimen and the maintenance dose regimen by using a pre-filled syringe filled with a formulation containing ofatumumab at a concentration of 20-300 mg/ml.

12. The method according to claim 10, wherein the autoinjector is loaded with a formulation containing ofatumumab at a concentration of 50 mg/ml.

13. The method according to claim 11, wherein the pre-filled syringe is filled with a formulation containing ofatumumab at a concentration of 50 mg/ml.

14. The method according to claim 1, wherein the loading dose regimen achieves B-cell depletion levels of ≤8 cells/µl in the patient.

15. The method according to claim 1, wherein the maintenance dose regimen keeps B-cell depletion level below 8 cells/µl in the patient.

16. The method according to claim 1, wherein the treatment alleviates or delays progression of the symptoms of MS.

17. The method according to claim 1, wherein the treatment slows progression of MS.

18. The method according to claim 1, wherein the patient has relapsing multiple sclerosis.

\* \* \* \* \*